US011980433B2

(12) United States Patent
Zhang et al.

(10) Patent No.: US 11,980,433 B2
(45) Date of Patent: May 14, 2024

(54) IN-VIVO MICRO-ROBOT FOR NERVE STRETCHING

(71) Applicants: THE FIRST MEDICAL CENTER CHINESE PLA GENERAL HOSPITAL, Beijing (CN); Shandong University, Jinan (CN)

(72) Inventors: Lihai Zhang, Beijing (CN); Rui Song, Beijing (CN); Ye Peng, Beijing (CN); Fuxin Du, Beijing (CN); Shuwei Zhang, Beijing (CN); Yanqiang Lei, Beijing (CN); Gongzi Zhang, Beijing (CN)

(73) Assignees: THE FIRST MEDICAL CENTER CHINESE PLA GENERAL HOSPITAL, Beijing (CN); Shandong University, Jinan (CN)

( * ) Notice: Subject to any disclaimer, the term of this patent is extended or adjusted under 35 U.S.C. 154(b) by 0 days.

(21) Appl. No.: 17/971,663

(22) Filed: Oct. 24, 2022

(65) Prior Publication Data
US 2023/0045225 A1    Feb. 9, 2023

Related U.S. Application Data

(63) Continuation of application No. PCT/CN2021/109891, filed on Jul. 30, 2021.

(51) Int. Cl.
*A61B 34/32* (2016.01)
*A61B 17/00* (2006.01)

(52) U.S. Cl.
CPC .... *A61B 34/32* (2016.02); *A61B 2017/00345* (2013.01); *A61B 2017/00734* (2013.01); *A61B 2017/00876* (2013.01)

(58) Field of Classification Search
CPC ............................ A61B 34/30; A61B 34/32
USPC ...................................................... 128/899
See application file for complete search history.

(56) References Cited

U.S. PATENT DOCUMENTS

| 6,132,360 | A | * | 10/2000 | Halpern | A61N 2/00 |
| | | | | | 128/898 |
| 7,147,647 | B2 | * | 12/2006 | Onyekaba | A61B 17/1128 |
| | | | | | 606/152 |
| 2003/0204197 | A1 | * | 10/2003 | Onyekaba | A61B 17/1128 |
| | | | | | 606/152 |
| 2009/0253954 | A1 | | 10/2009 | Katayama | |

(Continued)

FOREIGN PATENT DOCUMENTS

CN    102188286 A    9/2011
CN    103533898 A    1/2014
(Continued)

*Primary Examiner* — John R Downey

(57) ABSTRACT

Disclosed is an in-vivo micro-robot for nerve stretching, comprising a channel, and a movable part and a fixed part located at the channel. The movable part is disposed to be movable along the channel, the movable part sleeves the fixed part and is used for driving the fixed part to move along the channel, and the fixed part is connected to a nerve to be stretched. The in-vivo micro-robot is embedded into a patient's body through surgery, so that the extension of the nerve is accelerated and is regular and quantitative, thereby effectively solving the problems of small probability of nerve self-repair and long recovery period in traditional nerve bridging surgery.

17 Claims, 6 Drawing Sheets

(56) References Cited

U.S. PATENT DOCUMENTS

2009/0254088 A1* 10/2009 Soubeiran .......... A61B 17/7216
                                                              606/63
2010/0234863 A1*  9/2010 Zhang .................. D01D 5/0007
                                                              606/152
2014/0277001 A1*  9/2014 Swain ............... A61F 13/00068
                                                              606/152

FOREIGN PATENT DOCUMENTS

| CN | 110269581 A | 9/2019 | |
| WO | WO-2009145116 A1 * | 12/2009 | ............. A61B 90/02 |
| WO | 2010056716 A2 | 5/2010 | |

* cited by examiner

Front ← → Rear

IN-VIVO MICRO-ROBOT FOR NERVE STRETCHING

TECHNICAL FIELD

The present invention belongs to the technical field of medical appliances, and relates to an in-vivo micro-robot for nerve stretching.

BACKGROUND

In traditional treatment means, neurotmesis caused by open cutting injuries, gunshot penetrating injuries, severe traction injuries and the like needs to be connected by nerve bridging surgery. The bridging method is generally to construct a degradable tubular stent and mix various factors for promoting nerve growth in the stent to repair and reconstruct the nerve defect. However, this method can only allow the nerve to grow itself, with a long growth cycle and the risk of recovery failure.

Existing studies have shown that mechanical stretching of nerves during nerve repair can accelerate nerve repair, and the deficiency in the traditional nerve bridging surgery can be made up by promoting tissue growth with growth factors. Patent No. CN104178422B discloses a nerve axon stretching and growing device, comprising a culture and stretching control system and a mechanical device. A stretching membrane and a bottom membrane can be coated with electrode contacts, and connected to a multichannel nerve signal recording and stimulating system for recording nerve signals of axons and selectively stimulating different sites. In terms of stretching time and safety, it is more appropriate to embed a micro-robot into a patient's body than to stretch the nerve through an in-vitro appliance.

Therefore, it is urgent to design an in-vivo micro-robot for nerve stretching to solve the existing technical problems.

SUMMARY

In view of the above technical problems, the present invention provides an in-vivo micro-robot for nerve stretching which has a reasonable structure. The robot is embedded into a patient's body through surgery, and mechanical stretching can be combined with growth promotion of growth factors, so that the extension of the nerve is accelerated and is quantitative, thereby effectively solving the problems of small probability of nerve self-repair and long recovery period in traditional nerve bridging surgery.

In order to solve the above technical problems, the present invention provides an in-vivo micro-robot for nerve stretching, comprising a channel, and a movable part and a fixed part located at the channel, where the movable part is disposed to be movable along the channel, the movable part sleeves the fixed part and is used for driving the fixed part to move along the channel, and the fixed part is connected to a nerve to be stretched.

As a preferred embodiment, the in-vivo micro-robot for nerve stretching further comprises an adjusting part, wherein the adjusting part is connected to the fixed part, and is located at a front end of the movable part for limiting a displacement of the movable part.

As a preferred embodiment, the movable part is provided with an electromagnet, the fixed part is provided with a permanent magnet, and the movable part is connected to the fixed part through a spring assembly.

As a preferred embodiment, an inner side wall of the channel is provided with sliding slots, wedge-shaped tables are arranged in the sliding slots, the movable part and the fixed part are provided with abutting plates, and the abutting plates abut against the wedge-shaped tables.

As a preferred embodiment, the fixed part comprises a mandrel, a rear baffle of the spring assembly, the permanent magnet, a rear support, a tail and a suture loop;

the mandrel is concentrically disposed in the channel; and a rear end of the mandrel is sequentially sleeved with the rear baffle of the spring assembly, the permanent magnet, the rear support and the tail, the rear baffle of the spring assembly, the permanent magnet, the rear support and the tail are in interference fit with the mandrel, the suture loop is connected to the tail, and the nerve to be stretched is connected to the suture loop.

As a preferred embodiment, the movable part comprises a front support, the electromagnet, a front baffle and a spring of the spring assembly; the electromagnet comprises a coil and an iron core;

the front support is connected to a front end of the iron core, the iron core sleeves the mandrel and is located on a rear side of the front support, and an outer peripheral side of the iron core is provided with the coil; and the front baffle and the spring of the spring assembly sleeve the outer peripheral side of the iron core, the front baffle of the spring assembly is fixedly connected to the iron core, and the front support and the iron core are in clearance fit with the mandrel.

As a preferred embodiment, the adjusting part comprises an adjusting ring, and the adjusting ring is integrally connected to the front end of the mandrel through threads.

As a preferred embodiment, outer peripheral sides of the front support and the rear support are provided with the abutting plates, the inner side wall of the channel is provided with the sliding slots, and a magnetic field formed by energization of the coil and the permanent magnet repel each other such that the abutting plates of the front support are pushed to move forward along the sliding slots to stretch the nerve.

As a preferred embodiment, the abutting plates extend from the front end to the rear end of the mandrel and are obliquely disposed toward the outer side.

As a preferred embodiment, after the electromagnet is energized, the movable part moves forward along the channel to drive the spring of the spring assembly to extend; and after the electromagnet is deenergized, the spring of the spring assembly is restored to drive the fixed part to move forward along the channel.

As a preferred embodiment, the in-vivo micro-robot for nerve stretching further comprises a limiting sleeve sleeving the outer peripheral side of the mandrel and located between the front baffle of the spring assembly and the rear baffle of the spring assembly.

As a preferred embodiment, the number of the sliding slots in the channel is matched with the number of the abutting plates of the front support and the rear support, the wedge-shaped tables are arranged in the sliding slot, and the wedge-shaped tables are disposed in a length direction of the sliding slot.

As a preferred embodiment, the tail comprises a connecting piece and a clamping piece that are of a tubular structure and are integrally formed, an inner side wall of the clamping piece is provided with the clamping slot, the clamping piece is further provided with a pressing hole, and the pressing hole is disposed in a radius direction of the clamping piece and located in the clamping slot.

As a preferred embodiment, the suture loop comprises a ring portion and a connecting portion, the connecting portion is disposed on one side of the ring portion, the connecting portion is provided with a protrusion, the connecting portion is inserted into the clamping slot, and the protrusion is clamped into the pressing hole.

As a preferred embodiment, the protrusion is disposed on an outer side of the connecting portion, the connecting portion is further provided with a notch, and the notch is disposed close to a joint of the connecting portion and the ring portion and located on an inner side of the connecting portion.

As a preferred embodiment, the mandrel is internally provided with a chamber, and a control portion is disposed in the chamber to realize on-off control of the coil; and a power supply is further arranged in the chamber to supply power for the coil and the control portion.

As a preferred embodiment, the power supply and the control portion can be designed into a hollow form and a solid form, and the hollow form is used for reserving a space for nerve self-growth.

As a preferred embodiment, the control portion comprises a microcontroller, an electromagnetic circuit and a protection circuit, the microcontroller controls on-off frequency and time of the electromagnetic circuit, and the protection circuit is used for ensuring normal operation of the control portion.

As a preferred embodiment, the adjusting ring is capable of adjusting a step length of the displacement of the movable part within 0-1.5 mm through threads.

As a preferred embodiment, the iron core is connected to the front support through a rivet.

As a preferred embodiment, the front support and the rear support are made of polytetrafluoroethylene or other biocompatible materials.

The present invention has the following beneficial effects:

The in-vivo micro-robot for nerve stretching provided by the present invention has a reasonable structure. The robot is embedded into a patient's body through surgery, and mechanical stretching can be combined with growth promotion of growth factors, so that the extension of the nerve is accelerated and is quantitative, thereby effectively solving the problems of small probability of nerve self-repair and long recovery period in traditional nerve bridging surgery.

BRIEF DESCRIPTION OF THE DRAWINGS

The above advantages of the present invention will become clearer and easier to understand through the detailed description made in conjunction with the following accompanying drawings. These accompanying drawings are only schematic and do not limit the present invention.

In the accompanying drawings, the components represented by reference symbols are as follows:

1. Front support; 2. Spring assembly; 2a-1. Front baffle; 2a-2. Rear baffle; 2b. Spring; 3. Iron core; 4. Coil; 5. Permanent magnet; 6. Rear support; 7. Tail; 7a. Connecting piece; 7b. Clamping piece; 7c. Clamping slot; 7d. Pressing hole; 8. Suture loop; 8a. Ring portion; 8b. Connecting portion; 8c. Protrusion; 8d. Notch; 9. Adjusting ring; 10. Channel; 10a. Sliding slot; 10b. Wedge-shaped table; 11. Nerve; 12. Mandrel; 12-1. Hollow mandrel; 13. Limiting sleeve; 14. Control portion; 14-1. Hollow control portion; 15. Power supply; 15-1. Hollow power supply; 16. Abutting plate.

DETAILED DESCRIPTION

The present invention will be described in detail below in conjunction with specific embodiments and accompanying drawings.

The embodiments described here are particular specific embodiments of the present invention to illustrate the concept of the present invention. They are all explanatory and exemplary, and should not be construed as limiting the embodiments of the present invention or the scope of the present invention. In addition to the embodiments described herein, those skilled in the art can also adopt other obvious technical solutions based on the contents disclosed in the claims and description of the present application, comprising technical solutions adopting any obvious replacements and modifications made to the embodiments described herein.

The accompanying drawings in the description are schematic diagrams to assist in explaining the concept of the present invention, and schematically show the shape of parts and the relationship therebetween. It should be noted that in order to clearly show the structure of components of the embodiments of the present invention, the accompanying drawings are not drawn according to the same scale. The same reference signs are used to denote the same parts.

Figure 1:
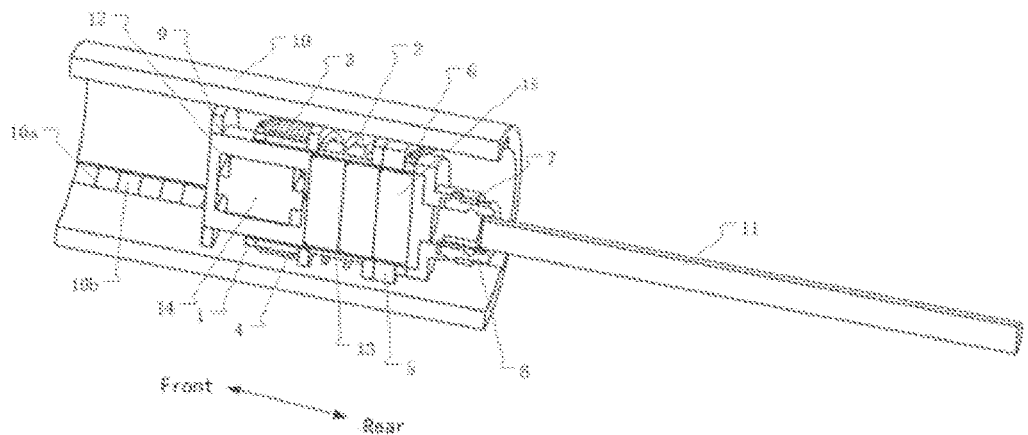
FIG. 1 is a sectional view of the in-vivo micro-robot for nerve stretching according to the present invention.
Figure 2:
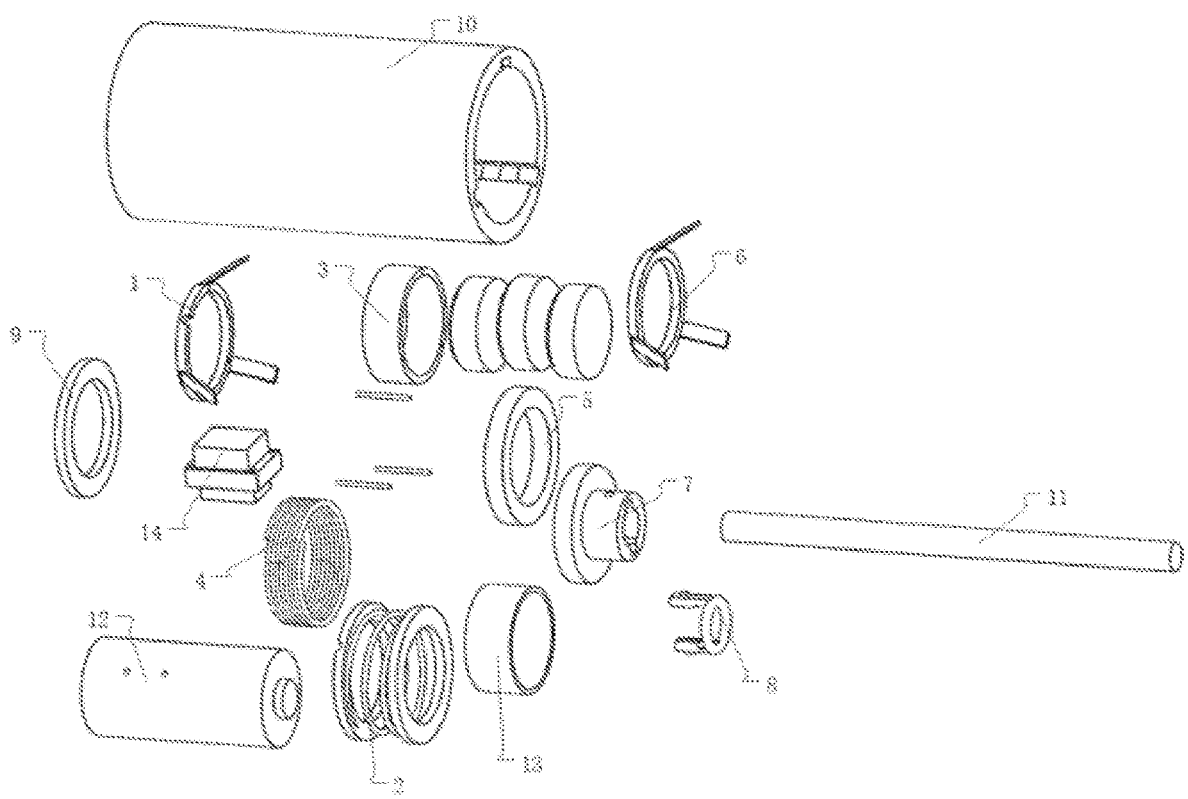
FIG. 2 is an exploded view of components of the in-vivo micro-robot according to the present invention.

Structural schematic diagrams of an in-vivo micro-robot for neural stretching of the present application are shown in FIG. 1 to FIG. 2. The in-vivo micro-robot comprises a channel 10, and a movable part and a fixed part located at the channel 10. The movable part is disposed to be movable along the channel, the movable part sleeves the fixed part and is used for driving the fixed part to move along the channel 10, and the fixed part is connected to a nerve to be stretched.

Further, the in-vivo micro-robot further comprises an adjusting part. The adjusting part is connected to the fixed part, and is located at the front end of the movable part for limiting the displacement of the movable part.

In the embodiment shown in FIG. 1, the fixed part comprises a mandrel 12, a rear baffle 2a-2 of the spring assembly 2, a permanent magnet 5, a rear support 6, a tail 7 and a suture loop 8, and the mandrel 12 is concentrically disposed in the channel 10. The rear end of the mandrel 12 is provided with the suture loop 8, the suture loop 8 is connected to the mandrel 12 through the tail 7, and the nerve to be stretched is connected to the suture loop 8.

As a preferred embodiment, the movable part comprises a front support 1, a coil 4, a front baffle 2a-1 and a spring 2b of the spring assembly 2, and an iron core 3. The coil 4 and the iron core 3 constitute a part of the electromagnet.

The front support 1 is connected to a front end of the iron core 3, the iron core 3 sleeves the mandrel 12 and is located on the rear side of the front support 1, and an outer peripheral side of the iron core 3 is provided with the coil 4. The front baffle 2a-1 of the spring assembly 2 is fixedly connected to the iron core 3, and the front support 1 and the iron core 3 are slidable on the mandrel 12.

As a preferred embodiment, the adjusting part comprises an adjusting ring 9, and the adjusting ring 9 is integrally connected to the front end of the mandrel 12 through threads.

As a preferred embodiment, outer peripheral sides of the front support 1 and the rear support 6 are provided with abutting plates 16, the inner side wall of the channel 10 is provided with sliding slots 10a, and a magnetic field formed by energization of the coil 4 and the permanent magnet 5 repel each other such that the abutting plates 16 of the front support 1 are pushed to move forward along the sliding slots 10a to stretch the nerve.

Specifically, after the coil 4 is energized, the front support 1 moves forward to drive the spring 2b to extend. After the coil 4 is deenergized, the spring 2b is restored to drive the rear support 6 to move forward.

Further, the permanent magnet 5 can be a rubidium magnet or other types of magnets.

Figure 3:
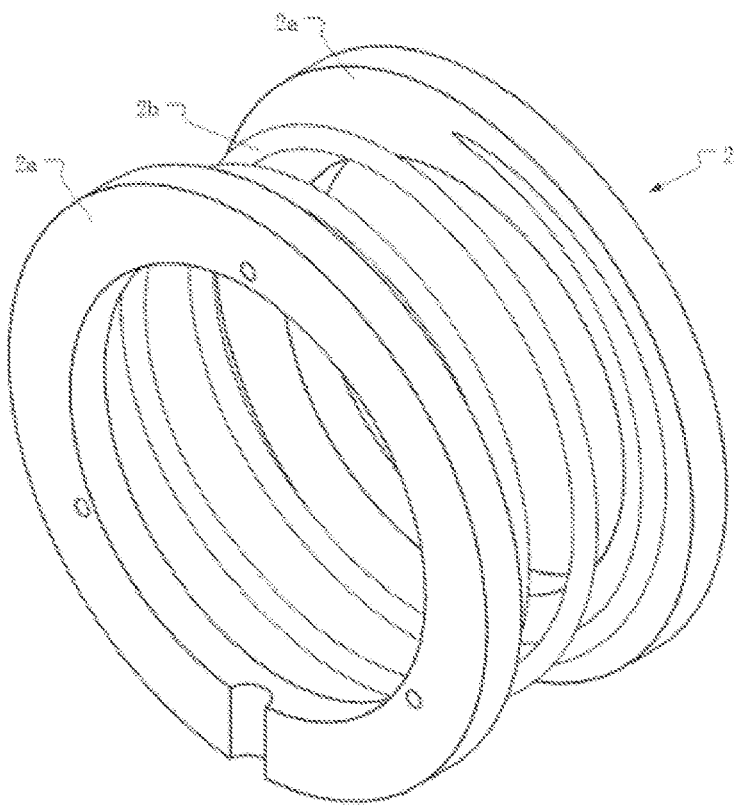
FIG. 3 is a structural schematic diagram of the spring assembly according to the present invention.

FIG. 3 is a structural schematic diagram of the spring assembly according to the present invention. The spring assembly 2 comprises the front baffle 2a-1, the rear baffle 2a-2 and the spring 2b, and the spring 2b is connected between the front baffle 2a-1 and the rear baffle 2a-2. After the coil 4 is energized, the front support 1 moves forward to drive the spring 2b to extend. After the coil 4 is deenergized, the spring 2b is restored to drive the rear support 6 to move forward.

As one embodiment of the present invention, the in-vivo micro-robot further comprises a limiting sleeve 13 sleeving the outer peripheral side of the mandrel 12 and located between the front baffle 2a-1 and the rear baffle 2a-2. The limiting sleeve 13 can limit extension and retraction of the spring 2b and control an amount of movement of the in-vivo micro-robot.

Figure 9:
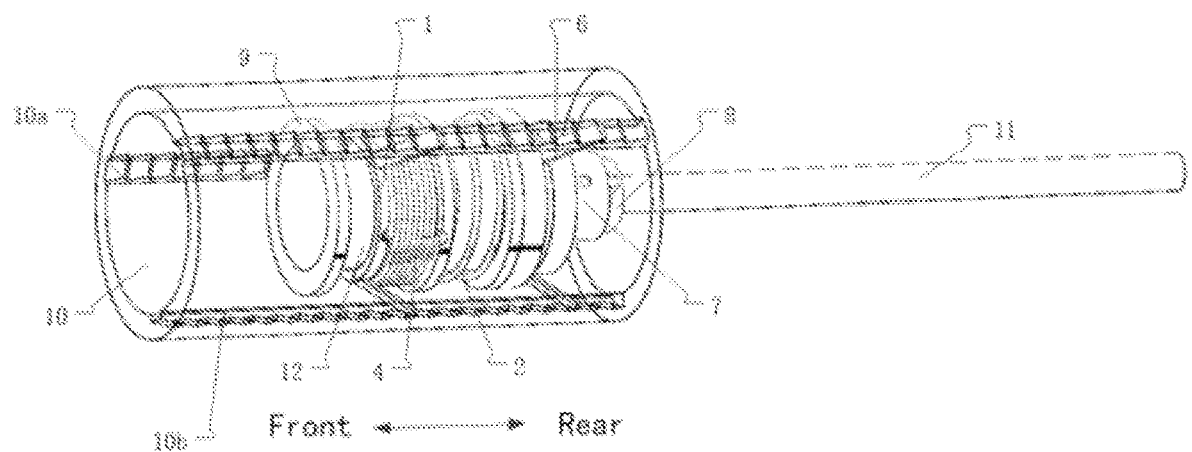
FIG. 9 is a schematic diagram of the in-vivo micro-robot after the channel is transparently displayed according to the present invention.

In the present invention, the number of the sliding slots 10a in the channel 10 is matched with the number of the abutting plates 16 of the front support 1 and the rear support 6, wedge-shaped tables 10b are arranged in the sliding slot 10a, a cross section of the wedge-shaped table 10b is in a right-angled triangle, an inclined surface of the wedge-shaped table 10b faces the tail 7, the plurality of wedge-shaped tables 10b are in the shape of teeth, the abutting plates 16 of the front support 1 and the rear support 6 abut against the teeth, as shown in FIG. 1 and FIG. 9, and the wedge-shaped tables 10b are disposed in a length direction of the sliding slot 10a.

Figure 4:
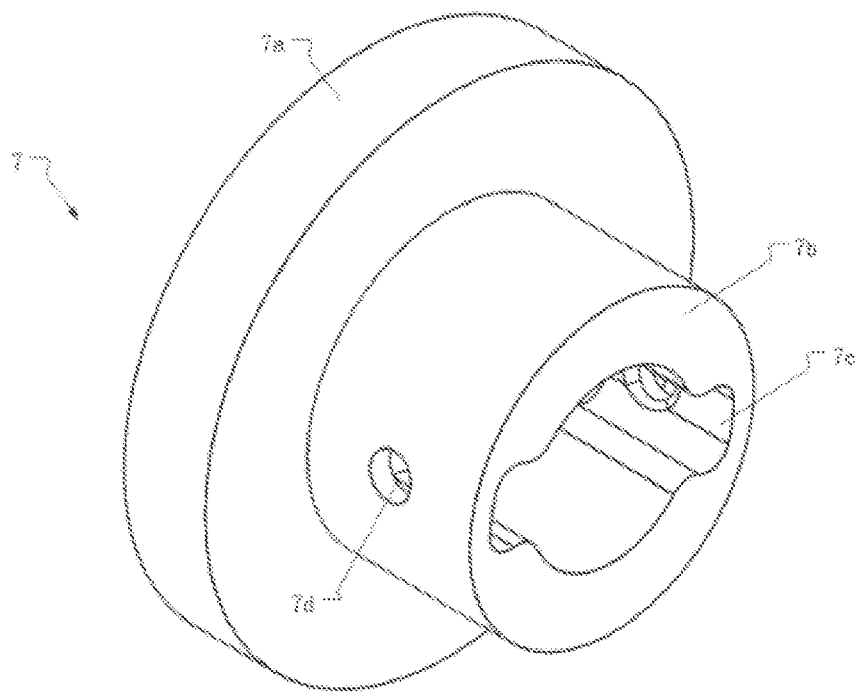
FIG. 4 is a structural schematic diagram of the tail according to the present invention.

As another embodiment of the present invention, the tail 7 comprises a connecting piece 7a and a clamping piece 7b that are of a tubular structure and are integrally formed, as shown in FIG. 4. The inner side wall of the clamping piece 7b is provided with a clamping slot 7c, the clamping piece 7b is further provided with pressing holes 7d, and the pressing hole 7d is disposed in a radius direction of the clamping piece 7b and located in the clamping slot 7c.

Figure 5:
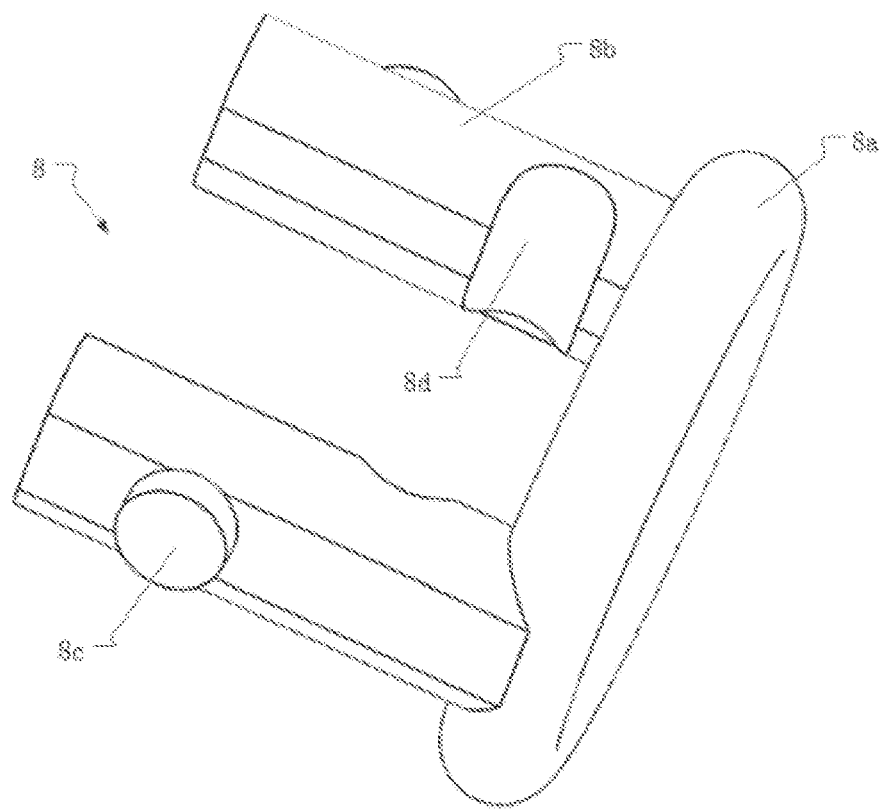
FIG. 5 is a structural schematic diagram of the suture loop according to the present invention.

Further, the suture loop 8 comprises a ring portion 8a and connecting portions 8b, as shown in FIG. 5, the connecting portion 8b is disposed on one side of the ring portion 8a, the connecting portion 8b is provided with a protrusion 8c, the connecting portion 8b is inserted into the clamping slot 7c, and the protrusion 8c is clamped into the pressing hole 7d.

The protrusion 8c is disposed on the outer side of the connecting portion 8b, the connecting portion 8b is further provided with a notch 8d, and the notch 8d is disposed close to a joint of the connecting portion 8b and the ring portion 8a and located on the inner side of the connecting portion 8b. The arrangement of the notches 8d can enhance the flexibility of the connecting portions 8b, and facilitate pressing of the protrusions 8c by the operator, so as to realize the bending of the connecting portions 8b and realize the separation of the suture loop 8 from the tail 7.

In the embodiment shown in FIG. 1, the mandrel 12 is internally provided with a chamber, and a control portion 14 is disposed in the chamber to realize on-off control of the coil 4. A power supply 15 is further arranged in the chamber to supply power for the coil 4 and the control portion 14. The control unit 14 can control the time and number of times of the energization, so as to achieve the purpose of manually controlling the nerve extension length. The control portion 14 can be a PIC10F series microcontroller, and the power supply 15 is an SR416SW button cell.

Figure 10:
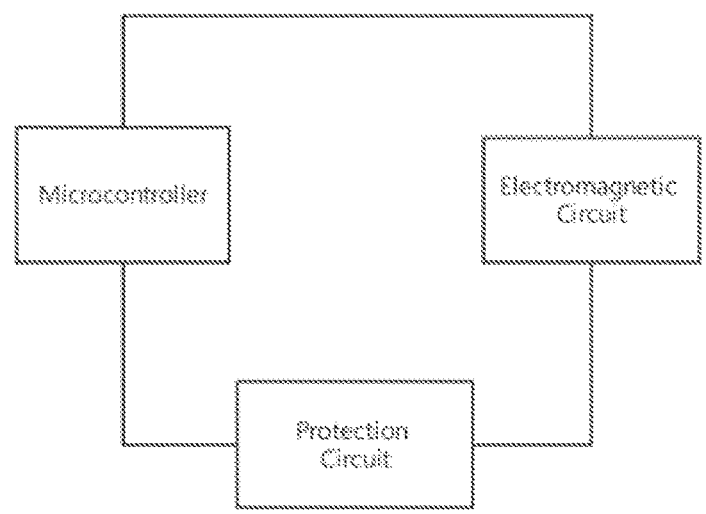
FIG. 10 is an electrical block diagram of the control portion according to the present invention.

FIG. 10 is an electrical block diagram of the control portion according to the present invention. The control portion comprises a microcontroller, an electromagnetic circuit and a protection circuit, the microcontroller controls on-off frequency and time of the electromagnetic circuit, and the protection circuit is used for ensuring normal operation of the control portion.

Figure 11:
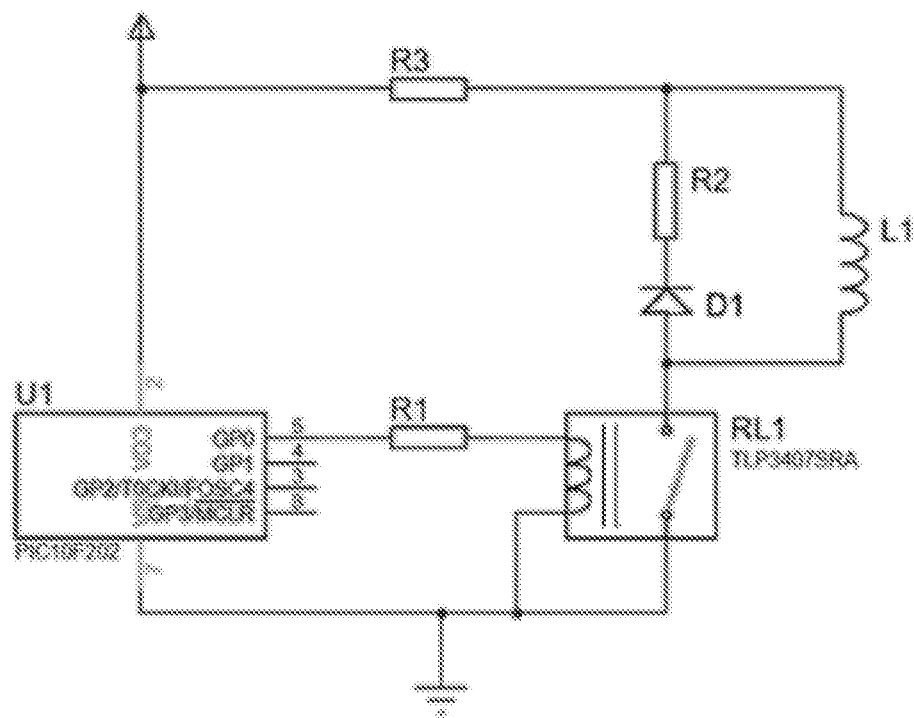
FIG. 11 is a schematic diagram of one embodiment of the control portion according to the present invention.

FIG. 11 is an electrical control diagram of one embodiment of the control portion according to the present invention. U1 is the microcontroller, L1 is the electromagnet and is represented by an inductance symbol in the circuit, resistors R1 and R3 are used to control magnitude of a current and protect the circuit, and constitute a discharge loop protection circuit with R2 and D1. The discharge loop protection circuit uses a single-chip microcomputer to control the on-off of a relay, thereby controlling an energization state of the electromagnet L1. Specifically, when a switch at a working end of the relay RL1 is in an open state, a high level is applied to a control end of the relay through GP0, so that the switch at the working end of the relay is closed, and the electromagnet is energized. When the working end of the relay RL1 is in a closed state, a low level is applied to the relay through GP0, so that the switch at the working end of the relay RL1 is opened, and the electromagnet L1 loses magnetism.

Figure 12:
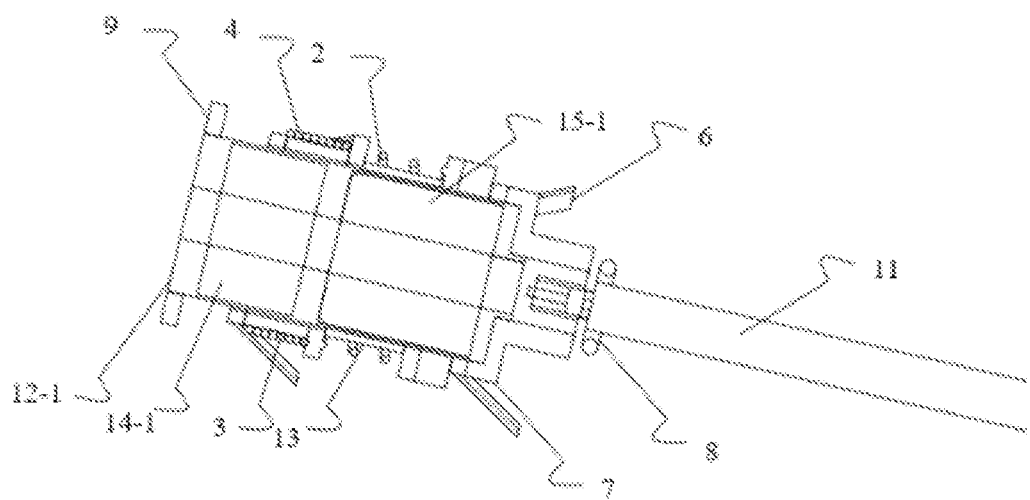
FIG. 12 is a sectional view of the power supply and the control portion in hollow arrangement according to the present invention.

FIG. 12 shows the power supply and the control portion in a hollow arrangement form according to the present invention. The hollow arrangement form comprises a hollow power supply 15-1, a hollow control portion 14-1 and a hollow mandrel 12-1, and is used for providing a space for nerve self-growth.

Further, the adjusting ring 9 is threadedly connected to the front end of the mandrel 12, and is capable of adjusting a distance from the front support by rotation so as to adjust a step length of the displacement of the front support along the channel within 0-1.5 mm.

In order to reliably control the reliable movement of the in-vivo micro-robot, the rear baffle 2a-2 of the spring assembly, the permanent magnet 5, the rear support 6 and the tail 7 are in interference fit with the mandrel, the front support 1 and the iron core 3 are in clearance fit with the mandrel 12, and a clearance between the iron core 3 and the mandrel 12 is 0.1 mm-2 mm.

In the present invention, the iron core 3 is connected to the front support 1 through a rivet, the iron core 3 is correspondingly provided with a mounting hole in the length direction, and the front support 1 is provided with a fixing hole, so that the rivet connects the front support 1 and the iron core 3 into an integral body through the fixing hole of the front support 1 and the mounting hole of the iron core 3.

Figure 6:
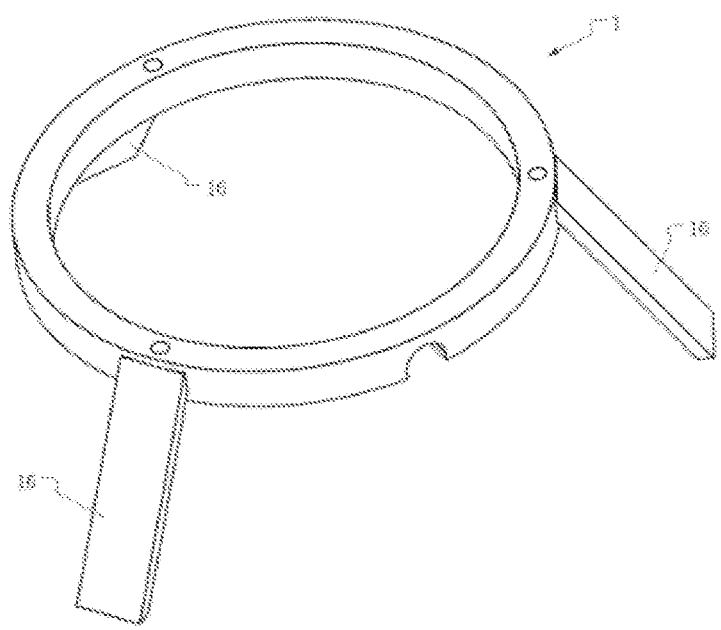
FIG. 6 is a structural schematic diagram of the front support according to the present invention.
Figure 7:
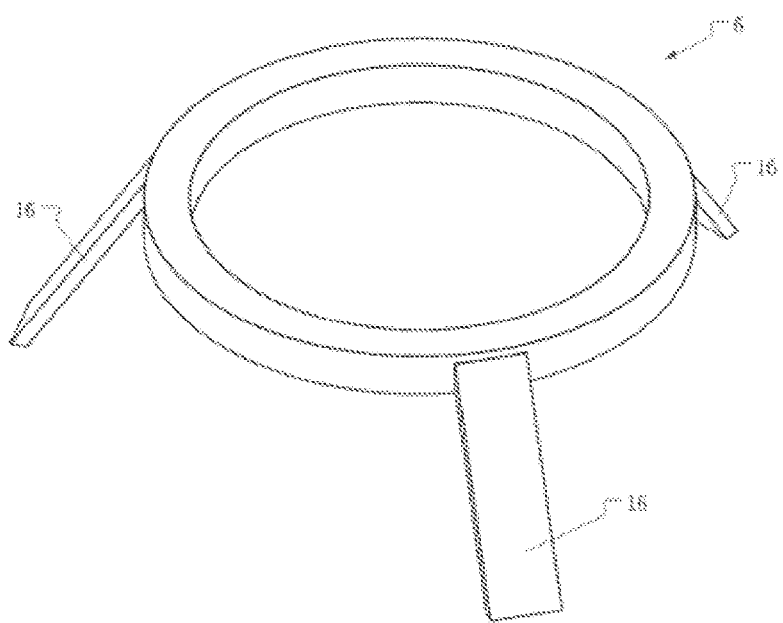
FIG. 7 is a structural schematic diagram of the rear support according to the present invention.
Figure 8:
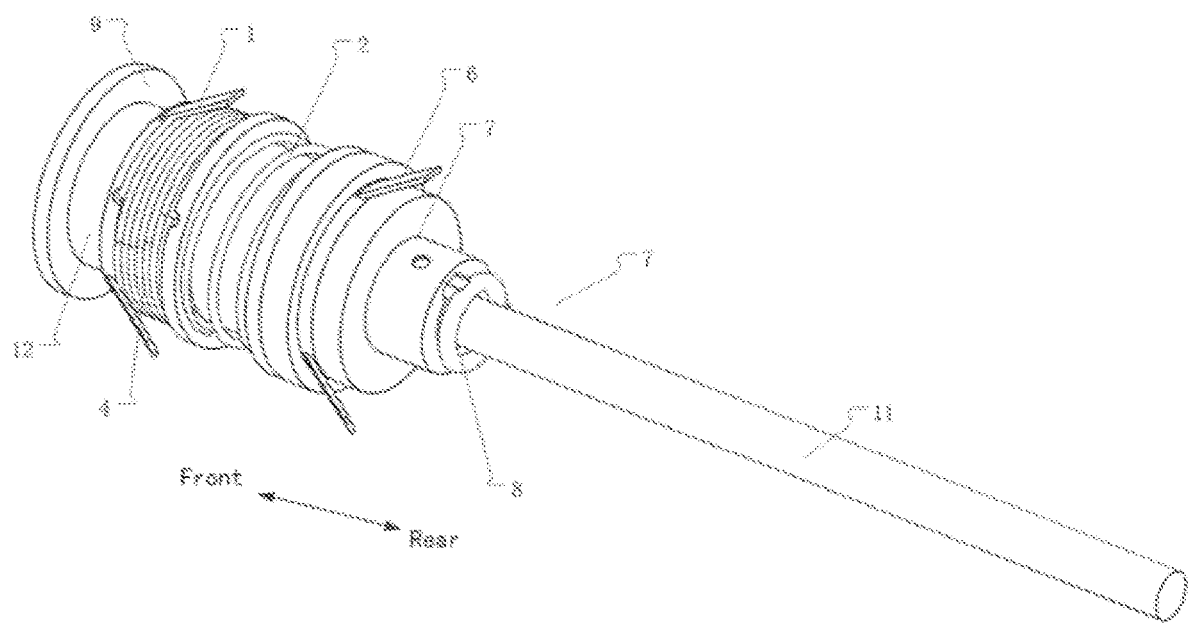
FIG. 8 is a structural schematic diagram of the in-vivo micro-robot without the channel according to the present invention.

The front support 1 and the rear support 6 are made of a biocompatible material, as shown in FIG. 6 and FIG. 7, and the abutting plates 16 extend from the front end to the rear end of the mandrel and are obliquely disposed toward the outer side. Corresponding main body plates of the front support 1 and the rear support 6 are annular plates, and the abutting plates 16 are uniformly distributed along the center of the annular plate to ensure that the front support 1 and the rear support 6 stably move in an axial direction of the channel 10.

Working principle: the robot is embedded into a patient's body through surgery, a nerve 11 is sutured to the suture loop 8, the magnetic field formed by the energization of the coil 4 on the iron core 3 and the permanent magnet 5 repel each other to generate a forward repulsive force such that the front support 1 is pushed forward by one unit length (which is controlled by the adjusting part, and can be n wedge-shaped table lengths, n being an integer greater than or equal to 1), and the abutting plates 16 of the front support abut against the next wedge-shaped table 10b. After the energization is stopped, the repulsive force disappears. The spring pulls the fixed part to advance, the rear support 6 advances by one unit length, and at the same time, the suture loop 8 stretches the nerve 11 to advance. At this point, the nerve is stretched forward by one unit length ((which can be n wedge-shaped table lengths, n being an integer greater than or equal to 1)). In addition, the microcontroller controls the time and number of times of the energization of the electromagnet, thereby achieving the purpose of manually and quantitatively controlling the nerve extension length. While the nerve grows under the long-time action of the stretching, the nerve also grows spontaneously. The robot is arranged in a hollow form, thereby achieving the purpose of reserving a space for nerve self-growth.

Compared with the defects and deficiencies of the prior art, the in-vivo micro-robot for nerve stretching provided by the present invention has a reasonable structure. The robot is embedded into a patient's body through surgery, and mechanical stretching can be combined with growth promotion of growth factors, so that the extension of the nerve is accelerated and quantitative, thereby effectively solving the problems of small probability of nerve self-repair and long recovery period in traditional nerve bridging surgery.

The present invention is not limited to the above-described embodiments, and anyone can obtain other products in various forms under the enlightenment of the present invention. However, regardless of any changes in its shape or structure, any technical solutions that are the same as or similar to those of the present application fall within the protection scope of the present invention.

The invention claimed is:

1. An in-vivo micro-robot for nerve stretching, comprising a channel, and a first movable part and a second movable part located at the channel, wherein the first movable part is disposed to be movable along the channel, the first movable part sleeves the second movable part and is used for driving the second movable part to move along the channel, and the second movable part is sized and configured to be connected to a nerve to be stretched to fix the nerve to be stretched;

wherein the second movable part comprises a mandrel, a rear baffle of a spring assembly, a permanent magnet, a rear support, a tail and a suture loop;

the mandrel is concentrically disposed in the channel; and a rear end of the mandrel is sequentially sleeved with the rear baffle of the spring assembly, the permanent magnet, the rear support and the tail, the rear baffle of the spring assembly, the permanent magnet, the rear support and the tail are in interference fit with the mandrel, the suture loop is connected to the tail, and the suture loop is configured to be connected to the nerve to be stretched.

2. The in-vivo micro-robot according to claim 1, further comprising an adjusting part, wherein the adjusting part is connected to the second movable part, and is located at a front end of the first movable part for limiting a displacement of the first movable part.

3. The in-vivo micro-robot according to claim 2, characterized in that the first movable part is provided with an electromagnet, and the first movable part is connected to the second movable part through a spring assembly.

4. The in-vivo micro-robot according to claim 3, characterized in that an inner side wall of the channel is provided with sliding slots, a wedge-shaped table is arranged in the sliding slot, the first movable part and the second movable part are respectively provided with abutting plates, and the abutting plates abut against the wedge-shaped table.

5. The in-vivo micro-robot according to claim 1, characterized in that the first movable part comprises a front support, the electromagnet, and a front baffle and a spring of the spring assembly; the electromagnet comprises a coil and an iron core;

the front support is connected to a front end of the iron core, the iron core sleeves the mandrel and is located on a rear side of the front support, and an outer peripheral side of the iron core is provided with the coil; and the front baffle and the spring of the spring assembly sleeve the outer peripheral side of the iron core, the front baffle of the spring assembly is fixedly connected to the iron core, and the front support and the iron core are in clearance fit with the mandrel.

6. The in-vivo micro-robot according to claim 5, characterized in that the adjusting part comprises an adjusting ring, and the adjusting ring is integrally connected to the front end of the mandrel through threads.

7. The in-vivo micro-robot according to claim 6, characterized in that after the electromagnet is energized, the first movable part moves forward along the channel to drive the spring of the spring assembly to extend; and after the electromagnet is deenergized, the spring of the spring assembly is restored to drive the second movable part to move forward along the channel.

8. The in-vivo micro-robot according to claim 7, further comprising a limiting sleeve sleeving the outer peripheral side of the mandrel and located between the front baffle of the spring assembly and the rear baffle of the spring assembly.

9. The in-vivo micro-robot according to claim 6, characterized in that outer peripheral sides of the front support and the rear support are provided with the abutting plates, the inner side wall of the channel is provided with the sliding slots, and a magnetic field formed by energization of the coil and the permanent magnet repel each other such that the abutting plates of the front support are pushed to move forward along the sliding slots to stretch the nerve.

10. The in-vivo micro-robot according to claim 9, characterized in that the abutting plates extend from the front end to the rear end of the mandrel and are obliquely disposed toward the outer side, and the abutting plates are capable of being elastically deformed under the acting force of the forward movement direction of the sliding slot.

11. The in-vivo micro-robot according to claim 9, characterized in that a number of the sliding slots in the channel is matched with a number of the abutting plates of the front support and the rear support, the wedge-shaped tables are arranged in the sliding slot, and the wedge-shaped tables are disposed in a length direction of the sliding slot.

12. The in-vivo micro-robot according to claim 11, characterized in that the tail comprises a connecting piece and a clamping piece that are of a tubular structure and are integrally formed, an inner side wall of the clamping piece is provided with a clamping slot, the clamping piece is further provided with a pressing hole, and the pressing hole is disposed in a radius direction of the clamping piece and located in the clamping slot.

13. The in-vivo micro-robot according to claim 12, characterized in that the suture loop comprises a ring portion and a connecting portion, the connecting portion is disposed on one side of the ring portion, the connecting portion is provided with a protrusion, the connecting portion is inserted into the clamping slot, and the protrusion is clamped into the pressing hole.

14. The in-vivo micro-robot according to claim 13, characterized in that the protrusion is disposed on an outer side of the connecting portion, the connecting portion is further provided with a notch, and the notch is located on an inner side of the connecting portion.

15. The in-vivo micro-robot according to claim 14, characterized in that the mandrel is internally provided with a chamber, and a control portion is disposed in the chamber to realize on-off control of the coil; and a power supply is further arranged in the chamber to supply power for the coil and the control portion.

16. The in-vivo micro-robot according to claim 15, characterized in that the control portion, the mandrel and the power supply are arranged to be of a hollow structure to reserve a space for nerve self-growth.

17. The in-vivo micro-robot according to claim 16, wherein the control portion comprises a microcontroller, an electromagnetic circuit and a protection circuit, the microcontroller controls on-off frequency and time of the electromagnetic circuit, and the protection circuit is used for ensuring normal operation of the control portion.

* * * * *